(12) United States Patent
Limbach et al.

(10) Patent No.: US 9,770,708 B2
(45) Date of Patent: Sep. 26, 2017

(54) OXIDATIVE ESTERIFICATION CATALYST

(71) Applicant: Rohm and Haas Company, Philadelphia, PA (US)

(72) Inventors: Kirk W. Limbach, Collegeville, PA (US); Dmitri A. Kraptchetov, Collegeville, PA (US); Christopher D. Frick, Collegeville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/905,988

(22) PCT Filed: Jul. 29, 2014

(86) PCT No.: PCT/US2014/048657
§ 371 (c)(1),
(2) Date: Jan. 19, 2016

(87) PCT Pub. No.: WO2015/017430
PCT Pub. Date: Feb. 5, 2015

(65) Prior Publication Data
US 2016/0151770 A1 Jun. 2, 2016

Related U.S. Application Data

(60) Provisional application No. 61/859,526, filed on Jul. 29, 2013.

(51) Int. Cl.

| | | |
|---|---|---|
| *B01J 21/04* | (2006.01) | |
| *B01J 21/08* | (2006.01) | |
| *B01J 21/12* | (2006.01) | |
| *B01J 23/06* | (2006.01) | |
| *B01J 23/10* | (2006.01) | |
| *B01J 27/14* | (2006.01) | |
| *B01J 27/186* | (2006.01) | |
| *B01J 37/02* | (2006.01) | |
| *B01J 37/16* | (2006.01) | |
| *B01J 23/644* | (2006.01) | |
| *B01J 23/648* | (2006.01) | |
| *B01J 23/652* | (2006.01) | |
| *B01J 27/045* | (2006.01) | |
| *C07C 67/39* | (2006.01) | |

(52) U.S. Cl.
CPC ......... *B01J 27/186* (2013.01); *B01J 23/6447* (2013.01); *B01J 23/6482* (2013.01); *B01J 23/6484* (2013.01); *B01J 23/6525* (2013.01); *B01J 27/045* (2013.01); *B01J 37/0242* (2013.01); *B01J 37/0244* (2013.01); *B01J 37/16* (2013.01); *C07C 67/39* (2013.01)

(58) Field of Classification Search
CPC ... B01J 21/04; B01J 21/08; B01J 21/12; B01J 21/14; B01J 21/18; B01J 23/06; B01J 23/10; B01J 23/18; B01J 23/22; B01J 23/28; B01J 23/31; B01J 23/44; B01J 23/6447; B01J 23/6482; B01J 23/6484; B01J 27/02; B01J 27/045; B01J 27/14; B01J 27/186
USPC ....... 502/240, 246–249, 251, 255, 262, 263, 502/302–304, 311, 312, 327, 329, 333, 502/339, 354, 355
See application file for complete search history.

(56) References Cited

U.S. PATENT DOCUMENTS

| | | | |
|---|---|---|---|
| 4,329,513 A | 5/1982 | Aoshima et al. | |
| 4,407,733 A * | 10/1983 | Birkenstock | B01J 23/40 502/174 |
| 4,518,796 A | 5/1985 | Aoshima et al. | |
| 4,714,695 A | 12/1987 | Paparizos et al. | |
| 5,892,102 A | 4/1999 | Mikami et al. | |
| 5,969,178 A | 10/1999 | Okamoto et al. | |
| 6,040,472 A | 3/2000 | Yamamatsu et al. | |
| 6,107,515 A | 8/2000 | Yamaguchi et al. | |
| 6,228,800 B1 | 5/2001 | Yamaguchi et al. | |
| 6,506,930 B1 | 1/2003 | Venter et al. | |
| 7,326,806 B2 | 2/2008 | Hayashi et al. | |
| 2006/0030728 A1 | 2/2006 | Schroeder | |
| 2011/0184206 A1 | 7/2011 | Suzuki et al. | |
| 2013/0190527 A1* | 7/2013 | Zhou | C07C 29/149 560/265 |

FOREIGN PATENT DOCUMENTS

| | | |
|---|---|---|
| CN | 1207959 A | 2/1999 |
| CN | 1485133 A | 3/2004 |
| CN | 101073784 A | 11/2007 |
| CN | 101190866 A | 6/2008 |
| CN | 102049255 A | 5/2011 |
| DE | 19734242 A1 | 2/1999 |
| EP | 1226868 A1 | 7/2002 |
| JP | H05148184 A | 6/1993 |
| JP | H10263399 A | 10/1998 |
| JP | 2001233828 A | 8/2001 |
| JP | 2004137173 A | 5/2004 |
| JP | 2004345973 A | 12/2004 |
| WO | 2012035637 A1 | 3/2012 |

* cited by examiner

OTHER PUBLICATIONS

Li, et al; Effects of La, Ce and Pr on Catalytic Performance O Catalysts for the Oxidative Sterification of Methacrolein; Chemical Research and Application, vol. 21, Period 4; Apr. 4, 2009.

*Primary Examiner* — Patricia L Hailey
(74) *Attorney, Agent, or Firm* — Edward L. Brant

(57) ABSTRACT

A catalyst comprising palladium, bismuth, and at least one third element X selected from the group consisting of P, S, Sc, V, Ga, Se, Y, Nb, Mo, La, Ce, and Nd, wherein the catalyst further comprises a support.

10 Claims, No Drawings

OXIDATIVE ESTERIFICATION CATALYST

BACKGROUND OF THE INVENTION

The invention relates to a catalyst that is useful for the preparation of carboxylic acid esters via oxidative esterification.

The production of methyl methacrylate (MMA) from methacrolein (MAC), methanol, and oxygen is known. For example, U.S. Pat. No. 6,040,472 discloses this reaction using a palladium (Pd)-lead (Pb) crystalline structure, $Pd_3Pb_1$, on a silica support that has minor alumina and magnesia components. However, the Pd—Pb catalyst is capable of producing undesirably high amounts of methyl formate as a by-product. U.S. Pat. No. 4,518,796 discloses the use of a Pd-bismuth (Bi) catalyst. However, that catalyst did not give high MMA selectivity, which is desired for this reaction.

U.S. Pat. No. 5,892,102 discloses MAC oxidative esterification catalysts that include Pd—Bi—X intermetallics, where X can be a variety of elements, on a ZnO or $CaCO_3$. These supports are undesirable from a mechanical stability, likely acid resistance, and long-term catalyst life standpoint.

It would be desirable to have a non-Pb catalyst for selectively producing MMA while producing very little methyl formate by-product, thereby avoiding the issues associated with Pb-containing waste streams.

SUMMARY OF THE INVENTION

The catalyst of the invention is such a catalyst comprising palladium, bismuth, and at least one third element X selected from the group consisting of P, S, Sc, V, Ga, Se, Y, Nb, Mo, La, Ce, and Nd wherein the catalyst further comprises a support.

Surprisingly, the catalyst of the invention provides a high yield of MMA when used in the production of MMA from MAC via oxidative esterification, and may provide low levels of methyl formate by-product in that process.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The catalyst is a heterogeneous, porous catalyst. The catalyst comprises palladium, bismuth and at least one third element X selected from the group consisting of P, S, Sc, V, Ga, Se, Y, Nb, Mo, La, Ce, and Nd. Preferably, X is Y and/or Ga. In one embodiment of the invention, X comprises Ce and/or Mo. Combinations of X may be employed.

Preferably, any catalytic metal is in the reduced state, namely zero valency, and not in the cationic state, and may be present in the reduced state or as compounds. The catalytic elements are present in the reaction system in such a form that they can have some interaction with each other. For example, palladium, bismuth and X may form an alloy, or have some other interaction, such as an intermetallic compound.

The catalytic elements may be supported on a carrier, such as activated carbon, magnesium oxide, zinc oxide, titanium oxide, calcium carbonate, silica or alumina, and the amount of the catalytic constituents supported on the carrier advantageously may be from 0.1 to 20% by weight, preferably 1 to 10% by weight, based on the weight of the carrier. In one embodiment of the invention, the carrier comprises at least one of silica, alumina, and silica-alumina. Examples of carriers include pyrogenic silica, silica gel, alpha alumina and gamma alumina. The catalyst constituents may also be used in the metallic form or in the form of compounds without supporting them on a carrier. The ratio of palladium to bismuth in the catalyst is preferably 1:0.05 to 1:10 (atomic ratio). The ratio of X to bismuth is advantageously from 1:01 to 1:10, and in one embodiment of the invention is about 1:1. The carrier may be modified, as is known by those skilled in the art. For example, a silica carrier may be modified with alumina and/or magnesia. Combinations of carriers may be employed.

The catalyst can be prepared in a conventional manner. For example, a soluble salt such as palladium chloride can be reduced with a reducing agent such as formalin in aqueous solution to deposit metallic palladium and the deposited metallic palladium can be filtered to prepare a metallic palladium catalyst, or a suitable carrier can be impregnated with an aqueous acidic solution of a soluble palladium salt and the impregnated carrier is subjected to reduction with a reducing agent to prepare a supported palladium catalyst. In one embodiment of the invention, when it is intended to prepare a catalyst in which palladium, bismuth and at least one third element X, are supported on a carrier, a suitable carrier is impregnated with an aqueous solution of a soluble palladium salt, and the impregnated carrier is reduced with a suitable reducing agent, after which the reduced carrier is immersed in an aqueous solution of bismuth compound and a third compound, which is a compound of X, and evaporated to dryness and dried. Alternatively, the catalyst may be prepared by first supporting the bismuth compound on the carrier, then impregnating the carrier with palladium and at least one third compound, and thereafter adding a reducing agent, such as hydrazine.

As the bismuth compound used in the preparation of the above catalyst, any suitable bismuth-containing compound may be used. For example, fatty acid salts of bismuth, such as bismuth acetate, bismuth stearate, and the like can be employed. Other suitable compounds include bismuth oxide; bismuth hydroxide; and bismuth nitrate. These bismuth compounds may be anhydrous or may be in the form of a hydrate. As the third compound used in the preparation of the above catalyst, any suitable X-containing compound may be used. Examples of X-containing compounds include, using yttrium as a representative member of X, yttrium acetate, yttrium chloride hexahydrate, and yttrium sulfate. In one embodiment of the invention, yttrium nitrate is employed as the source of yttrium.

The catalyst may be subjected to activation and/or regeneration, as is known to those skilled in the art. For example, U.S. Pat. No. 6,040,472 discloses various catalyst activation techniques.

The catalyst of the invention may be employed in the oxidative esterification of aldehydes, such as MAC, with an alcohol, such as methanol, and an oxygen-containing gas. For example, the catalyst is useful in the preparation of MMA via oxidative esterification.

Methanol is widely commercially available. Methacrolein can be produced by various industrial scale processes, as known by those skilled in the art. See, e.g., U.S. Pat. Nos. 4,329,513 and 5,969,178.

The ratio of methanol fed to the amount of methacrolein fed in the reaction of this invention is not particularly limited, and the reaction may be conducted over a wide range of molar ratios such as 1:10 to 1,000:1, preferably from 1:1 to 10:1 methanol to methacrolein.

The oxygen-containing gas may be either oxygen gas or a mixed gas comprising oxygen gas and a diluent inert to the reaction such as, for example, nitrogen, carbon dioxide or the like. Air may be used as the oxygen-containing gas. The quantity of oxygen present in the reaction system advantageously is not less than the stoichiometric quantity required for the reaction, and preferably is not less than 1.2 times the stoichiometric quantity. In one embodiment of the invention, the amount of oxygen present in the reaction system is from 1.2 to 2 times the stoichiometric quantity required. Hydrogen peroxide may be introduced into the reaction system as an oxidizer. The oxygen-containing gas can be introduced to the reaction system by an suitable means, as known by those skilled in the art. For example, the oxygen-containing gas can be introduced via a sparger or a pipe into a reactor. The simple method of blowing the oxygen-containing gas into the reaction system can be employed.

The catalyst is employed in a catalytic amount. The amount of the catalyst, i.e., catalytic elements and optional carrier, may be varied freely depending on the kind and amount of the starting materials, the method of preparing the catalyst, process operating conditions and the like, although the weight ratio of catalyst to the starting aldehyde generally is from 1:1000 to 20:1. Advantageously, the ratio of catalyst to aldehyde is from 1:100 to 2:1. However, the catalyst may be used in an amount outside these ranges.

The process for producing methyl methacrylate comprises contacting reactants comprising methacrolein, methanol and an oxygen-containing gas, under oxidative esterification conditions in the presence of the catalyst. In one embodiment of the invention, the reaction may be conducted using a slurry of the catalyst in the liquid phase in the reaction zone. The reaction may be conducted at a temperature of from 0° C. to 120° C., preferably from 40° C. to 90° C. The reaction may be conducted at reduced pressure, at atmospheric pressure, or at superatmospheric pressure. The reaction may be conducted at a pressure of from 0.5 to 20 atm absolute, preferably from 1 to 10 atm absolute. The reaction may be conducted in a batch, semi-batch or continuous manner. Advantageously, the reaction is conducted in the liquid phase.

A polymerization inhibitor can be employed in the process when the product is a polymerizable compound. A wide variety of inhibitors are known and commercially available. Examples of inhibitors include hydroquinone (HQ), phenothiazine (PTZ), the methyl ester of hydroquinone (MEHQ), 4-hydroxy-2,2,6,6-tetramethylpiperidine-n-oxyl (4-hydroxy TEMPO, or 4HT), methylene blue, copper salicylate, copper dialkyldithiocarbamates, and the like.

In the oxidative esterification of MAC to form MMA, the undesired formation of methyl formate consumes reactant methanol and oxygen and produces two moles of water for each mole of methyl formate. Water is undesirable because it is problematic to remove from the reaction mixture, may promote the formation of undesired oxides on the catalyst surface and may promote the formation of undesired by-product methacrylic acid. The formation of methacrylic acid consumes reactant methacrolein and reactant oxygen and may cause deactivation of the catalyst.

Surprisingly, the catalyst in various embodiments can be employed in the oxidative esterification of MAC to form MMA containing less than 2, less than 1, less than 0.8, less than 0.6, less than 0.4, less than 0.2, less than 0.1, less than 0.05 or less than 0.01 mole of methyl formate per mole of methyl methacrylate. In various embodiments of the invention, the catalyst is employed in said esterification to provide a yield of MMA of at least 90%, or at least 95%, or at least 98%, or at least 99%, based on methacrolein, where yield is calculated as the mathematical product of conversion times selectivity.

SPECIFIC EMBODIMENTS OF THE INVENTION

The following examples are given to illustrate the invention and should not be construed as limiting its scope. In the examples where conversion and selectivity are calculated, they are calculated ignoring a 5 hour activation period, during which selectivity is comparatively poor.

Example 1

Pd—Bi—Y Catalyst Preparation

A catalyst having 5 wt % Pd, 2 wt % Bi, and 1 wt % Y on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding yttrium nitrate 0.74 g to provide 1 wt % Y on a carrier basis, and then adding 20.0 grams of the Aldrich Pd/alumina. The slurry is stirred for 1 hour at 60° C., then 10.0 grams of hydrazine hydrate are added slowly, dropwise, and the resulting mixture is stirred for an additional 1 hour at 90° C. The resulting solids are then separated via vacuum filtration, washed with 500 ml of deionized water, and vacuum dried at 45° C. for 10 hours.

Example 2

Preparation of MMA with Pd—Bi—Y Catalyst

A 5 gram sample of the catalyst of Example 1 is placed in a glass reactor with a 100 g solution of 3.9 wt % methacrolein in methanol. The solution also contains, as polymerization inhibitor, ca. 50 ppm phenothiazine and ca. 50 ppm hydroquinone. The solution is heated with stirring to 40° C. at atmospheric pressure with 35 cc/min 8% $O_2$ in $N_2$ bubbling through it for 22 hours. The reactor is equipped with a dry ice condenser and impeller.

Conversion of MAC is 100%. Selectivity to methyl methacrylate is 98.8% based on MAC. Thus, the yield is calculated as 100%×98.8%=98.8%. Surprisingly, very little methyl formate and methacrylic acid are measured in the resulting product.

Calculation of Conversion and Selectivity:

As noted above, in the examples where conversion and selectivity are calculated, they are calculated ignoring a 5 hour activation period. The concentration of various constituents is obtained at the fifth hour of operation and the twenty second hour of operation. Condensate from the dry ice condenser is returned to the reactor, and the samples are dilute in nature. Organic vapor losses and changes to sample weight are assumed to be minimal. The reactor contents are analyzed via a gas chromatograph (GC) with a flame ionization detector (FID).

Methacrolein conversion is calculated as the moles of MAC reacted during the relevant time period (i.e. the moles of methacrolein present at the fifth hour minus the moles of methacrolein present at the twenty second hour) divided by the moles of methacrolein present at the fifth hour and is expressed as a percentage.

Selectivity to methyl methacrylate is calculated as the moles of methyl methacrylate made (from hour five to hour twenty two) divided by the moles of MAC consumed over that time period and is also expressed as a percentage.

Example 3

Preparation of MMA with Pd—Bi—Y Catalyst

The procedure of Example 2 is repeated except that the 100 g solution of methacrolein in methanol contains 4.0 wt % methacrolein, and except that the inhibitor is approximately 50 ppm 4-HT in combination with PTZ (approximately 10 ppm) and HQ (approximately 10 ppm).

Conversion of MAC is 100%. Selectivity to methyl methacrylate is above 99% based on MAC. Surprisingly, very little methyl formate and methacrylic acid are measured in the resulting product.

Example 4

Pd—Bi—Ga Catalyst Preparation

A catalyst having 5 wt % Pd, 2 wt % Bi, and 1 wt % Ga on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding gallium nitrate nonahydrate 1.14 g to provide 1 wt % Ga on a carrier basis, and then adding 20.0 grams of the Aldrich Pd/alumina. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 5

Preparation of MMA with Pd—Bi—Ga Catalyst

The procedure of Example 3 is repeated except that the 100 g solution of methacrolein in methanol contains 3.9 wt % methacrolein, and the catalyst of Example 4 is employed as the catalyst.

Conversion of MAC is 100%. Selectivity to methyl methacrylate is 96.8% based on MAC.

Example 6

Pd—Bi—Nb Catalyst Preparation

A catalyst having 5 wt % Pd, 2 wt % Bi, and 1 wt % Nb on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding niobium chloride 0.56 g to provide 1 wt % Nb on a carrier basis, and then adding 20.0 grams of the Aldrich Pd/alumina. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 7

Preparation of MMA with Pd—Bi—Nb Catalyst

The procedure of Example 3 is repeated except that the 100 g solution of methacrolein in methanol contains 4.9 wt % methacrolein, and the catalyst of Example 6 is employed as the catalyst.

Conversion of MAC is 90%. Selectivity to methyl methacrylate is 64.4% based on MAC.

Example 8

Pd—Bi—Mo Catalyst Preparation

A catalyst having 5 wt % Pd, 2 wt % Bi, and 1 wt % Mo on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding ammonium molybdate 0.39 g to provide 1 wt % Mo on a carrier basis, and then adding 20.0 grams of the Aldrich Pd/alumina. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 9

Preparation of MMA with Pd—Bi—Mo Catalyst

The procedure of Example 3 is repeated except that the 100 g solution of methacrolein in methanol contains 3.9 wt % methacrolein, and the catalyst of Example 8 is employed as the catalyst.

Conversion of MAC is 100%. Selectivity to methyl methacrylate is 84.4% based on MAC.

Example 10

Preparation of MMA with Pd—Bi—Mo Catalyst

The procedure of Example 3 is repeated except that the 100 g solution of methacrolein in methanol contains 4.8 wt % methacrolein, and the catalyst of Example 9 is employed as the catalyst.

Conversion of MAC is 100%. Selectivity to methyl methacrylate is 79.5% based on MAC.

Example 11

Pd—Bi—Ce Catalyst Preparation

A catalyst having 5 wt % Pd, 2 wt % Bi, and 1 wt % Ce on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding cerium nitrate hexahydrate 0.59 g to provide 1 wt % Ce on a carrier basis, and then adding 20.0 grams of the Aldrich Pd/alumina. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 12

Preparation of MMA with Pd—Bi—Ce Catalyst

The procedure of Example 3 is repeated except that the 100 g solution of methacrolein in methanol contains 4.7 wt % methacrolein, and the catalyst of Example 11 is employed as the catalyst.

Conversion of MAC is 100%. Selectivity to methyl methacrylate is 92.4% based on MAC.

Example 13

Pd—Bi—Nd Catalyst Preparation

A catalyst having 5 wt % Pd, 2 wt % Bi, and 1 wt % Nd on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding neodymium chloride hexahydrate 0.48 g to provide 1 wt % Nd on a carrier basis, and then adding 20.0 grams of the Aldrich Pd/alumina. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 14

Preparation of MMA with Pd—Bi—Nd Catalyst

The procedure of Example 3 is repeated except that the 100 g solution of methacrolein in methanol contains 4.7 wt % methacrolein, and the catalyst of Example 13 is employed as the catalyst.

Conversion of MAC is 93%. Selectivity to methyl methacrylate is 80.2% based on MAC. Conversion and selectivity are calculated ignoring a 5 hour activation period, during which selectivity is comparatively poor.

Example 15

Pd—Bi—Y Catalyst Preparation

A catalyst having 5 wt % Pd, 2 wt % Bi, and 1 wt % Y on an alumina carrier is prepared using 5 wt % Pd and 2 wt % Bi on alumina as a starting point. This material is made by first using incipient wetness impregnation of the nitrate salt of Pd followed by calcining in air at atmospheric pressure and for sufficient time to denitrify the material. Bi is then added to the material by incipient wetness impregnation of the nitrate salt of Bi followed by calcining in air at atmospheric pressure for sufficient time to denitrify that material. A slurry is prepared by dissolving 0.74 g of yttrium nitrate tetrahydrate to provide 1 wt % Y on a carrier basis, and then adding 20.0 grams of the Pd/Bi material. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 16

Preparation of MMA with Pd—Bi—Y Catalyst

The procedure of Example 3 is repeated except that the 100 g solution of methacrolein in methanol contains 4.5 wt % methacrolein, and the catalyst of Example 15 is employed as the catalyst. (Note: a disruption in the run caused a non-operating delay for several hours where heating, stirring, and gas flow were turned off and not operational. It is believed the reaction had come to completion before this disruption occurred.)

Conversion of MAC is 100%. Selectivity to methyl methacrylate is above 99% based on MAC.

Example 17

Pd—Bi—Y Catalyst Preparation

A catalyst having 5 wt % Pd, 2 wt % Bi, and 1 wt % Y on an alumina (silica-alumina) carrier is prepared using the 5 wt % Pd and 2 wt % Bi on alumina (silica-alumina) starting point material of Ex. 15. A slurry is prepared by dissolving 0.74 g of yttrium nitrate tetrahydrate to provide 1 wt % Y on a carrier basis, and then adding 20.0 grams of the Pd/Bi material. The slurry is stirred for 1 hour at 60° C., after which 10.0 grams of hydrazine hydrate are added slowly, dropwise, and stirred for an additional 1 hour at 90° C. The resulting solids are then separated via vacuum filtration, washed with 500 ml of deionized water, and vacuum dried at 45° C. for 10 hours.

Example 18

Preparation of MMA with Pd—Bi—Y Catalyst

The procedure of Example 3 is repeated except that the 100 g solution of methacrolein in methanol contains 4.5 wt % methacrolein, and the catalyst of Example 17 is employed as the catalyst. (Note: a disruption in the run caused a non-operating delay for several hours where heating, stirring, and gas flow were turned off and not operational. It is believed the reaction had come to completion before this disruption occurred.)

Conversion of MAC is 100%. Selectivity to methyl methacrylate is above 99% based on MAC.

Example 19

Pd—Bi—P Catalyst Preparation

A catalyst having 5 wt % Pd, 2 wt % Bi, and 1 wt % P on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding 0.60 g phosphoric acid to provide 1 wt % P on a carrier basis, and then adding 20.0 grams of the Aldrich Pd/alumina. The slurry is stirred for 1 hour at 60° C., and then 10.0 grams of hydrazine hydrate are added slowly, dropwise, and the resulting mixture is stirred for an additional 1 hour at 90° C. The resulting solids are then separated via vacuum filtration, are washed with 500 ml of deionized water, and are vacuum dried at 45° C. for 10 hours.

Example 20

Preparation of MMA with Pd—Bi—P Catalyst

The procedure of Example 3 is repeated except that the 100 g solution of methacrolein in methanol contains 1.4 wt % methacrolein, and the catalyst of Example 19 is employed as the catalyst.

Conversion of methacrolein is 38%. Selectivity to MMA is 30.9% based on methacrolein. Surprisingly, very little methyl formate and methacrylic acid are measured in the resulting product.

Example 21

Pd—Bi—Sc Catalyst Preparation

A catalyst having 5 wt % Pd, 2 wt % Bi, and 1 wt % Sc on an alumina carrier is prepared using Sigma Aldrich 5 wt % Pd on alumina as a starting point. A slurry is prepared by dissolving 0.90 grams of bismuth nitrate pentahydrate in 100 ml of deionized water, then adding 0.98 g scandium nitrate hexahydrate to provide 1 wt % Sc on a carrier basis, and then adding 20.0 grams of the Aldrich Pd/alumina. The slurry is stirred for 1 hour at 60° C., then 10.0 grams of hydrazine hydrate are added slowly, dropwise, and the resulting mixture is stirred for an additional 1 hour at 90° C. The resulting solids are then separated via vacuum filtration, are washed with 500 ml of deionized water, and are vacuum dried at 45° C. for 10 hours.

Example 22

Preparation of MMA with Pd—Bi—Sc Catalyst

The procedure of Example 3 is repeated except that the 100 g solution of methacrolein in methanol contains 4.4 wt % methacrolein, and the catalyst of Example 21 is employed as the catalyst.

Conversion of methacrolein is 39%. Selectivity to methyl methacrylate is 25.1% based on methacrolein.

What is claimed is:

1. A catalyst comprising palladium, bismuth, and at least one third element X selected from the group consisting of Y, Ga, and combinations thereof, wherein the catalyst further comprises a support, wherein the atomic ratio of palladium to bismuth in the catalyst is from 1:0.05 to 1:10.

2. The catalyst of claim 1 wherein the support comprises at least one of alumina and silica.

3. The catalyst of claim 1 wherein the support comprises alumina modified with magnesia.

4. The catalyst of claim 1 wherein the support comprises primarily silica.

5. The catalyst of claim 4 wherein the support is modified with alumina, magnesia, or a combination thereof.

6. The catalyst of claim 4 wherein the silica comprises primarily pyrogenic silica.

7. The catalyst of claim 1 wherein X is Y.

8. The catalyst of claim 1 wherein X is Ga.

9. The catalyst of claim 1 wherein the support is selected from the group consisting of activated carbon, magnesium oxide, zinc oxide, titanium oxide, calcium carbonate and combinations thereof.

10. The catalyst of claim 1 wherein the ratio of X to bismuth is from 1:0.1 to 1:10.

\* \* \* \* \*